United States Patent [19]

Mueller

[11] Patent Number: 5,101,655
[45] Date of Patent: Apr. 7, 1992

[54] APPARATUS AND METHOD FOR WEATHERSTRIP WEAR TESTING

[75] Inventor: William F. Mueller, Rochester, N.H.

[73] Assignee: Harvard Industries-The Kingston Warren Corp., Newfields, N.H.

[21] Appl. No.: 545,929

[22] Filed: Jun. 29, 1990

[51] Int. Cl.[5] .............................................. G01N 3/56
[52] U.S. Cl. ........................................ 73/7; 73/150 R
[58] Field of Search ................. 73/7, 10, 866, 865.9, 73/150 R, 150 A

[56] References Cited

U.S. PATENT DOCUMENTS

| | | | |
|---|---|---|---|
| 2,734,375 | 2/1956 | Galbraith et al. | 73/7 |
| 2,797,574 | 7/1957 | Rusca et al. | 73/7 |
| 3,364,726 | 1/1968 | Bonham | 73/7 |
| 4,416,951 | 11/1983 | Mesnel | 428/586 |
| 4,470,223 | 9/1984 | Mesnel | 49/441 |
| 4,505,224 | 3/1985 | Kranz | 118/636 |
| 4,551,376 | 11/1985 | Kessler | 428/85 |
| 4,789,703 | 12/1988 | Fabris et al. | 524/464 |
| 4,888,091 | 12/1989 | Nollen et al. | 162/109 |
| 5,038,625 | 8/1991 | Chan | 73/865.9 |

FOREIGN PATENT DOCUMENTS

| | | | |
|---|---|---|---|
| 2008083 | 9/1971 | Fed. Rep. of Germany | 73/7 |
| 172104 | 7/1965 | U.S.S.R. | 73/7 |
| 200867 | 10/1967 | U.S.S.R. | 73/7 |
| 360588 | 1/1973 | U.S.S.R. | 73/7 |
| 2075101A | 11/1981 | United Kingdom . | |
| 2081881A | 2/1982 | United Kingdom . | |
| 2082452A | 3/1982 | United Kingdom . | |
| 2150966A | 7/1985 | United Kingdom . | |

OTHER PUBLICATIONS

"Simple reciprocating friction and wear tester"; *Tribology international*; vol. 13, No. 1, pp. 11-15, Feb. 1980, D. F. Moore et al.

*Primary Examiner*—Tom Noland
*Attorney, Agent, or Firm*—Lahive & Cockfield

[57] ABSTRACT

An apparatus for evaluating the wear resistance of a weatherstripping of the kind applied to a motor vehicle window frame wherein a window can moveably engage the frame via the weatherstripping, the weatherstripping including a lubricating material, such as flocking, adhered to a base material, whereby the moveable engagement can cause wear of the adhered lubricating material. The apparatus includes first structure for holding a test strip of weatherstripping, a wand having a tapered nose portion, and second structure, coupled to the wand and first structure, for imposing a plurality of strokes of the wand nose portion upon the test strip. Third structure, coupled to the second structure, is for adjusting the amount of force with which the wand nose portion is sought to be imposed upon the test strip during the plurality of strokes. The wand is a thin, flat and elongate glass part having a tapered nose portion.

16 Claims, 1 Drawing Sheet

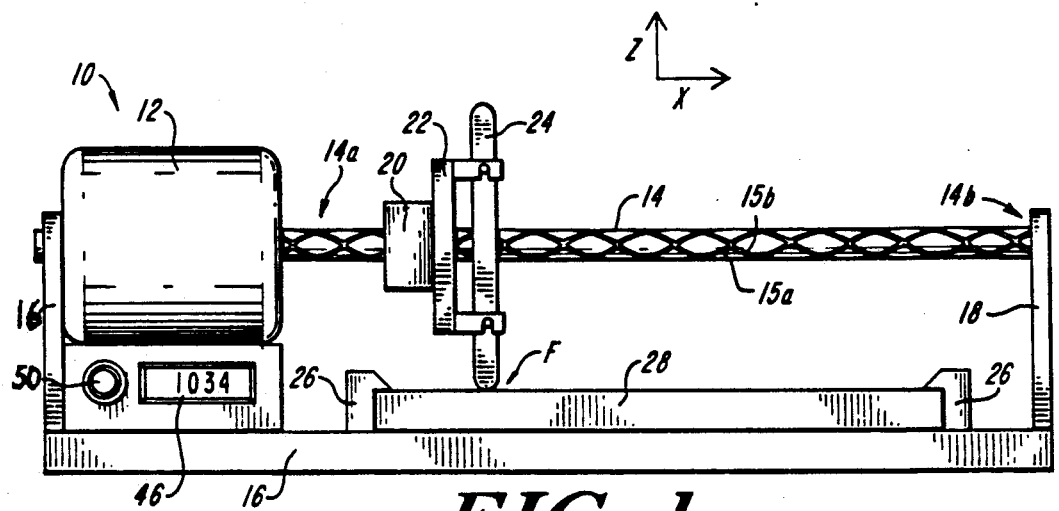
FIG. 1
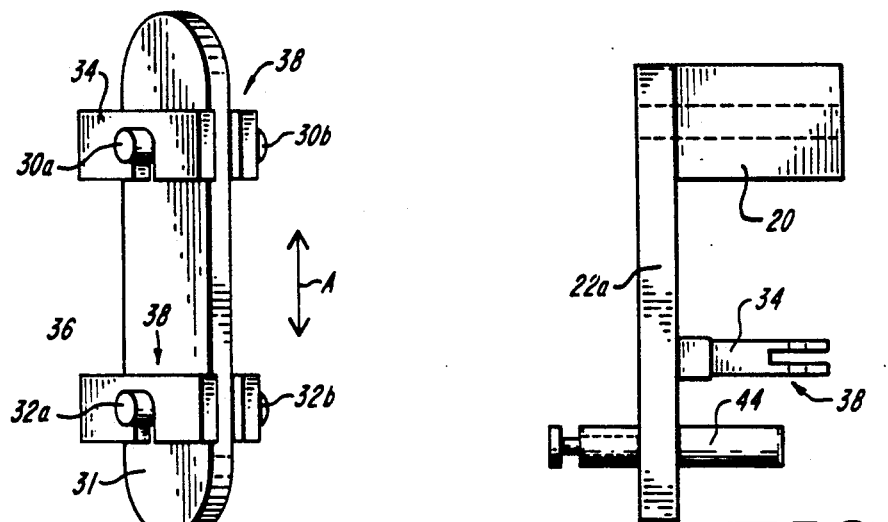
FIG. 2
FIG. 3
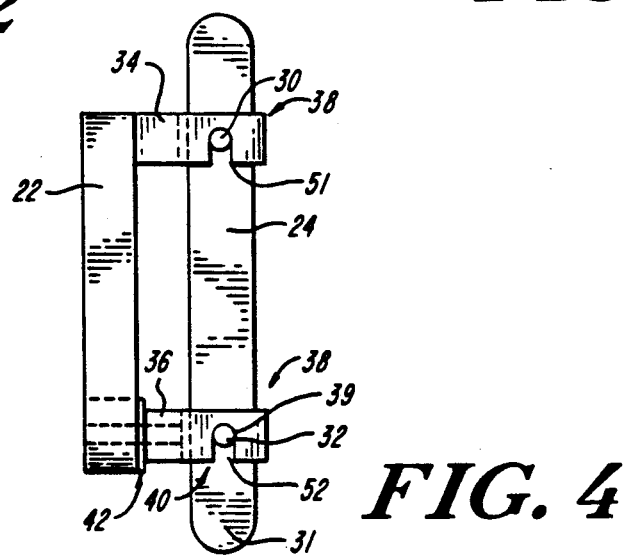
FIG. 4

APPARATUS AND METHOD FOR WEATHERSTRIP WEAR TESTING

BACKGROUND OF THE INVENTION

The present invention relates to wear testers, and more particularly, to wear resistance testers of the kind which subject a sample of weatherstripping to repeated wear cycles.

Wear testers, also known as wear resistance testers, are generally employed in evaluation of the durability of various products. For example, a fabric may be desired to have a certain minimum durability, and a wear tester may be useful in evaluating the durability (or wear resistance) of a particular formulation of such fabric. This can enable evaluation and refinement of a particular manufacturing method.

Extruded elastomeric weatherstrips are commonly used to provide sealing between the openings in motor vehicle bodies and closure elements (such as the glass window panes) for those openings. These seals help to provide an air and water barrier between the outside environment and that of the interior of the motor vehicle. Typical weatherstrips for window elements include a base material (such as rubber) and a resilient coating (such as a flocking) adhered to the base. The flocking acts as a dry lubricant to reduce the sliding resistance of the pane against the weatherstripping.

Flocking may be applied to a weatherstrip using a variety of techniques, e.g., by rolling a suitable adhesive onto the surface of the base material and then delivering the fibers to the adhesive for adhering the fibers thereto. If such adhering is accomplished within an electrostatic field, the fibers tend to stand on end so as to increase the effectiveness of their lubricating action. Often the flock fibers are of a synthetic material, such as nylon or dacron, of less than one millimeter in length.

The quality of attachment of the flocking to the base material, i.e., how well the flock fibers are adhesively secured to the base material, will determine the life of a particular formulation of flocking, adhesive and base material. As well, the quality and durability of the flock fiber itself will impact upon such life.

It is therefore an object of the present invention to provide a test apparatus which can adequately test in a controlled and reproducible manner the quality of a sample motor vehicle weatherstripping, such as may be useful in evaluating the durability of the flocking, the adhesive, and the base material of the sample.

SUMMARY OF THE INVENTION

The requirements associated with testing of weatherstripping are well met by the present invention, which is a wear resistance tester provided with special capability of calibration and replication of wear which it has induced upon a test sample of flocked motor vehicle weatherstripping.

In one aspect of the invention, an apparatus is disclosed for testing the wear resistance of a weatherstripping of the kind applied to a motor vehicle window frame. In use, a window can moveably engage the frame via the weatherstripping, where the weatherstripping includes a lubricating material adhered to a base material, and whereby the moveable engagement of window and frame can cause wear of the adhered material. The apparatus includes a first device for holding a test strip of flocked weatherstripping, a wand having a tapered nose portion, and a second device, coupled to the wand and first device, for imposing a plurality of strokes of the wand nose portion upon the test strip.

Embodiments of this aspect may include any of the following features:

The tester apparatus may include a third device, coupled to the second device, for adjusting the amount of force with which the wand nose portion is sought to be imposed upon the test strip. Preferably the wand is a thin, flat and elongate glass part, with the tapered nose portion defining a radius of ⅜ inch. The second device preferably has an upper arm and a lower arm to which the wand is attached, wherein the weight of the wand can be entirely supported horizontally and laterally by the upper arm and only lateral stress being supported by the lower arm. The second device is adjustable in elevation. The upper and lower arms respectively terminate in double-tined receivers, the receivers being configured to receive the wand. Preferably, the wand has a pair of upper and a pair of lower studs for coupling the wand to respective ones of the upper and lower arm double-tined receivers. Preferably the lower arm includes a load cell.

The apparatus may also include a double threaded shaft, ball reverser, or the like, coupled to a motor, and a travel bearing assembly which mates with the double threaded shaft, ball reverser, or the like, the latter driven in a given direction by the motor, and the travel bearing travelling accordingly with reciprocal motion such that each of said strokes begins with substantial acceleration up to a constant velocity and maintains said velocity substantially constant throughout a substantial portion of said stroke.

In another aspect of the invention, a method is disclosed for testing the wear resistance of a flocked weatherstripping of the kind applied to a motor vehicle window frame. In use, a window can moveably engage the frame via the weatherstripping, where the weatherstripping includes a flocking material adhered to a base material, and whereby said moveable engagement can cause wear of the adhered flocking. The method includes the steps of holding a test strip of flocked weatherstripping in holding means; coupling a wand having a nose portion to a second means for imposing a test regimen of a plurality of strokes of the wand nose portion upon the flocking of the test strip, the coupling being such that the weight of the wand is entirely supported by a first support means of the coupling means, while the wand is held laterally fixed by the first support means and a second support means of the coupling means; and adjusting the amount of force with which the wand nose portion is sought to be imposed upon the test strip during the first of the plurality of strokes, such that the amount of force during the last of said plurality of strokes less the amount of force during said first stroke is a net force which is indicative of the wear imparted upon the test strip by the wand nose portion during said plurality of strokes. The coupling step may include the step of placing the wand on a scale and adjusting the weight of the wand to a desired amount.

These and other advantages of the present invention will be more fully understood by reference to the following detailed description in conjunction with the attached drawing.

BRIEF DESCRIPTION OF THE DRAWINGS

FIG. 1 is a side view of an illustrative embodiment of the present invention.

FIG. 2 is a perspective view of a wand in cooperation with support arms of the invention.

FIG. 3 is a top view of the travel assembly of the invention.

FIG. 4 is a side view of the wand in cooperation with the support arms and holding fixture of the present invention.

DETAILED DESCRIPTION OF THE PREFERRED EMBODIMENT

An illustrative embodiment of a wear resistance tester in practice of the present invention is shown in the side view of FIG. 1. Wear resistance tester 10 is provided with a drive element 12 and a drive shaft/ball reverser 14 which is rotatably affixed to the drive element at shaft end 14a. Drive element 12 is mounted to housing 16. A far end 14b of shaft 14 is held in an endplate 18 affixed to housing 16. Hence, the drive element, which for example may take the form of an electric motor with a reduction gear, is poised to cooperate with the shaft to drive the shaft in a given direction with continuous motion.

Preferably shaft 14 bears reciprocating double threads 15a, 15b, such as in a conventional ball reverser. A travel assembly 20 is mounted to shaft 14. Preferably the travel assembly is internally threaded and cooperates with shaft 14 such that the travel assembly can be cycled from one shaft end to the other end and back again along shaft 14 (e.g., from end 14a to end 14b and back to end 14a) without changing direction of shaft rotation. However, other reciprocating arrangements are equally within the scope of the present invention.

A clamping frame 26 is provided affixed to housing 16 in a manner that a sample to be tested may be held and clamped in place by the clamping frame. The frame assures that the sample does not move or wrinkle while under test.

Travel assembly 20 includes a holding fixture 22, the latter being adjustable vertically along axis Z. A wand 24 is mounted to the holding fixture and is therefore also adjustable vertically. The wand 24 defines a longitudinal axis A as shown in FIG. 2 and is provided with studs 30a,b and 32a,b which extend perpendicular to axis A. Wand 24 is affixed to holding fixture 22 via these studs, with the wand's operative end 31 downwardly directed for contact with the test sample.

The wand is preferably thin, long and moderately wide, somewhat similar to a tongue depressor. The wand is also preferably made of glass, and terminates in a radius of ⅜ inch at its operative end 31. The purpose of this preferred configuration is generally so as to be able to replicate a piece of motor vehicle window glass rubbing up and down a weatherstripping in a motor vehicle window frame. In this manner, as closely as possible, typical wear of a flocked motor vehicle window stripping can be evaluated.

A counter 46 is provided which counts the cycles during which the glass wand has traversed from end 14a to end 14b and back to end 14a of shaft 14. A speed control 50 is provided to control the cycle rate.

In operation of the above embodiment, drive element 12 turns shaft 14, which threadly drives travel assembly 20 up and down shaft 14 along axis X. At the same time, the wand's operative end 31 is caused to repeatedly cycle along axis X in rubbing contact with test sample 28. Now, after a selected amount of rubbing cycles, which are tabulated by counter 46, the wear imposed upon the sample can be evaluated. Such items can be studied as the durability of the flock fiber itself, the quality of the adhesive bonding the flocking to the base, and/or the durability of the weatherstripping base material, for example.

Fixture 22 is shown in FIGS. 2-4. Fixture 22 includes a balance arm 22a. A weight block 44 is slidably coupled to arm 22a for purposes described below.

As shown in FIGS. 2, 3, 4, the holding fixture includes an upper arm 34 and a lower arm 36. Upper arm 34 is provided with a double-tined mounting station 38, for receipt of the wand and its upper mounting studs 30a,b. Lower arm 36 includes a double-tined mounting station 40 for receipt of the lower portion of the wand and lower studs 32a,b. Studs 30a,b and 32a,b respectively cooperate with the tines of arms 34 and 36 to enable wand 24 to be firmly attached to and held by the arms and holding fixture.

The weight of wand 24 is supported essentially by upper arm 34, with the lower arm being essentially unweighted at the beginning of a testing regime. By design, stud 30a seats entirely within slot 51 of upper arm 34; lower stud 32a merely mates with the sides of slot 52 with a gap 39 between the stud and the top of the slot. Hence, upper arm 34 carries the static weight of glass wand 24.

As the wand is conveyed horizontally along axis X during testing, wear forces F are applied from wand tip 31 to test sample 28 (see FIG. 1). This interaction of wand tip 31 and sample 28 causes wear of the sample.

A load cell 42 is preferably incorporated into fixture 22, between the fixture and lower arm 36. The load cell detects the sliding load (i.e., the resistance to sliding between the wand and sample) imposed on lower arm 36. The increase in this load during a testing regime is indicative of wear of the test sample 28, and can be represented by charting the changes in the output of the load cell.

The procedure for calibration and use of a preferred embodiment of the present invention is as follows. Resistance tester 10 is first put on its side (with the base toward the worker) so as to enable adjusting the position of weight block 44 on arm 22a. With the equipment turned in this position, the glass wand 24, when inserted in holding fixture 22, will hang essentially vertically. Hence, glass wand 22 is placed in the holding fixture with its radially terminated operative end 31 resting on a table scale. The holding fixture 22 is released relative to travel assembly 20 and the glass wand is adjusted in height so that it meets perpendicularly with the top of the scale. The fixture is then secured to the travel assembly.

With wand 24 adjusted along axis Z perpendicularly to the scale surface, the weight block 44 is adjusted in position on arm 22a until a desired reading is obtained. Preferably a reading of several hundred to a few thousand grams will be obtained and used in various test regimes. Next, as a precaution against breakage, the glass wand is temporarily removed from the holding fixture. Now the test machine 10 is placed in its original position with the base of the machine horizontal. A sample piece of weatherstrip 28 is placed in and clamped by clamping frame 26, with care being taken to ensure that the frame will not interfere with the cycling of the wand.

The glass wand is now re-installed in the holding fixture and is adjusted to be perpendicular to the weatherstrip sample, such as by releasing and then resecuring the fixture to the travel assembly. The counter 46 is reset to zero and the speed control 50 is adjusted to set the speed of reciprocation at preferably less than one cycle per second. Now the sample is tested for a desired number of cycles, with wear being noted upon examination of the worn sample. Such wear can be further monitored by charting the output of load cell 42, such as with a chart recorder. This will show the force (reading in pounds) of each cycle or group of cycles from time to time, as will readily indicate wear as an increas in the detected sliding force resulting for higher resistance between the wand tip and sample., The load cell can provide useful information regarding deterioration of the wand sample interface. However, the load cell will register acceleration. Therefore, preferably a shaft/ball reverser will be selected which accelerates rapidly up to a constant and even speed. Hence, upon a change of direction, a steady speed will be maintained essentially for a substantial length of the test sample for each stroke of the wand over the sample. This steady speed normalizes the output of the load cell, and makes its output easier to utilize, particularly if comparisons are restricted to data derived from the non-accelerated part of the wand's stroke over the sample.

The condition of end 31 of wand 24 should be evaluated and prepared from time to time. Resurfacing or cleaning end 31 can be done with a fine abrasive, such as 150 grit emery paper. End 31 should be resurfaced at least at the start of every test and/or every 5,000 cycles. If required, the wand can be reversed and the other end can be used.

The present inveniton is useful in testing the durability of a product coating on a support member. A preferred embodiment of the tester was used to test the durability of a flocked weatherstripping. The test enable determining both adhesion of the flock to the base and also the durability of the dacron fiber flock material. Nevertheless, the present wear tester may be employed for testing the characteristics of low friction coatings, ice-release chemicals, and various other compounds of interest.

Other embodiments are within the following claims.

What is claimed is:

1. Apparatus for evaluating the wear resistance of a weatherstripping of the kind applied to a motor vehicle window frame wherein a window can moveably engage the frame via the weatherstripping, the weatherstripping including a lubricating material adhered to a base material, whereby said moveable engagement can cause wear of the adhered lubricating material, the apparatus comprising
first means for holding a test strip of weatherstripping,
a wand having a tapered nose portion, and
second means, coupled to the wand and first means, for imposing a plurality of strokes of the wand nose portion upon the test strip, the second means including an upper arm and a lower arm to which the wan is attached, wherein the weight of the wand can be entirely supported by the upper arm.

2. The apparatus of claim 1 wherein the upper and lower arms respectively terminate in double-tined receivers, the receivers being configured to receive the wand.

3. The apparatus of claim 2 wherein the wand is a glass part having a respective pair of upper and lower studs for coupling the part to respective ones of the upper and lower arm double-tined receivers.

4. The apparatus of claim 3 wherein the lower arm includes a load cell.

5. The apparatus of claim 3 wherein the upper arm is configured to receive the upper studs so as to fully support the static weight of the wand.

6. The apparatus of claim 5 wherein the lower arm is configured to receive the lower studs without supporting the static weight of the wand.

7. The apparatus of claim 6 wherein the lower arm includes a load cell such that the sliding resistance between the test strip and wand nose portion can be charted.

8. Apparatus for evaluating the wear resistance of a weatherstripping of the kind applied to a motor vehicle window frame wherein a window can moveably engage the frame via the weatherstripping, the weatherstripping including a lubricating material adhered to a base material, whereby said moveable engagement can cause wear of the adhered lubricating material, the apparatus comprising
first means for holding a test strip of weatherstripping,
a wand having a tapered nose portion, and
second means, coupled to the wand and first means, for imposing a plurality of strokes of the wand nose portion upon the test strip, the second means including a rotary motor and a reciprocating device coupled to the motor, such that each of said strokes begins with substantial acceleration up to a constant velocity and maintains said velocity substantially constant throughout a substantial portion of said stroke.

9. The apparatus of claim 8 wherein the reciprocating device is a double threaded shaft or a ball reverser.

10. The apparatus of claim 8 wherein the second means further includes a travel bearing assembly which mates with the reciprocating device for reciprocal motion when the shaft is driven in a given direction by the motor.

11. Apparatus for testing the wear resistance of a flocked weatherstripping of the kind applied to a motor vehicle window frame wherein a window can moveably engage the frame via the weatherstripping, the weatherstripping including a flocking material adhered to a base material, whereby said moveable engagement can cause wear of the adhered flocking, the apparatus comprising
first means for holding a test strip of flocked weatherstripping,
a glass wand having a nose portion,
second means, coupled to the wand, for imposing a plurality of strokes of the wand nose portion upon the flocking of the test strip, wherein the second means further includes a reciprocating device coupled to the motor such that each of said strokes begins with substantial acceleration up to a constant velocity and maintains said velocity substantially constant throughout a substantial portion of said stroke, and
third means, coupled to the first means and the wand, for adjusting the amount of force with which the wand nose portion is sought to be imposed upon the test strip during said plurality of strokes.

12. A method for testing the wear resistance of a weatherstripping of the kind applied to a motor vehicle window frame wherein a window can moveably engage the frame via the weatherstripping, the weatherstripping including a lubricating material adhered to a base material, whereby said moveable engagement can cause wear of the lubricating material, the method comprising the steps of holding a test strip of lubricated weatherstripping in holding means, coupling a wand having a nose portion to a second means for imposing a plurality of strokes of the wand nose portion upon the lubricating material on the test strip, the second means including an upper arm and a lower arm to which the wand is attached, supporting the entire weight of the wand essentially by the upper arm at the commencement of the test, while the wand is held laterally fixed by the upper and lower arms, adjusting at the beginning of the test the amount of force with which the wand nose portion is sought to be imposed upon the test strip during said plurality of strokes, and measuring the amount of force exerted upon the lower arm during said plurality of strokes for correlating the measured amount of force to wear of the weatherstripping.

13. The method of claim 12 wherein the step of coupling includes the step of adjusting the weight of the wand to be a desired amount.

14. The method of claim 13 wherein the wand is a thin and elongate glass part having an operative end which terminates in a radius which defines the wand nose portion.

15. The method of claim 12 wherein the lubricating material is a flocking adhered to the base material.

16. The method of claim 12 wherein the each of said strokes begins with substantial acceleration up to a constant velocity and maintains said velocity substantially constant throughout a substantial portion of said stroke.

* * * * *